(12) United States Patent
Tseng

(10) Patent No.: US 6,732,731 B1
(45) Date of Patent: May 11, 2004

(54) MEDICAL MECHANICAL COMPRESSOR NEBULIZER

(75) Inventor: Daniel C. M. Tseng, Taipei Hsien (TW)

(73) Assignee: K-Jump Health Co., Ltd., Taipei Hsien (TW)

( * ) Notice: Subject to any disclaimer, the term of this patent is extended or adjusted under 35 U.S.C. 154(b) by 0 days.

(21) Appl. No.: 10/438,861

(22) Filed: May 16, 2003

(51) Int. Cl.⁷ .............................................. A61M 11/00
(52) U.S. Cl. ........................... 128/200.21; 128/200.14; 128/200.22; 128/203.12
(58) Field of Search ..................... 128/203.12, 203.15, 128/203.17, 203.26, 203.27, 203.28, 200.21, 200.22, 200.14; 604/58

(56) References Cited

U.S. PATENT DOCUMENTS 6,619,284 B2 * 9/2003 Kong ................... 128/200.21
6,637,432 B2 * 10/2003 Wakefield et al. ..... 128/203.23

OTHER PUBLICATIONS

US 2001/0002592 A1 (Attolini, Lorenzo) Jun. 7, 2001.*
US 2001/0037807 A1 (Kong, Geok Weng) Nov. 8, 2001.*

* cited by examiner

*Primary Examiner*—Glenn K. Dawson
*Assistant Examiner*—Michael Mendoza
(74) *Attorney, Agent, or Firm*—Birch, Stewart, Kolasch & Birch, LLP

(57) ABSTRACT

An improved medical mechanical compressor nebulizer for atomizing liquid inhalation dose to achieve therapeutic effect comprises a body, an air compression device located in the body, a safety switch which is serially connected to voltage is located at the surrounding of the air compression device and an atomization device connecting to the air compression device and an output device. The atomization device is precisely and securely fastened to the air compression device by a screwing mechanism, not only for connection of air passage, but also for forming a coupled air chamber which serves as a buffer to attain more stabilized ejecting air, reduce noise and achieve improved atomization effect. Also, the above screwing design can prevent unwarranted power consumption if the apparatus is inadvertently activated by the user.

6 Claims, 5 Drawing Sheets

MEDICAL MECHANICAL COMPRESSOR NEBULIZER

FIELD OF THE INVENTION

The present invention relates to an improved medical mechanical compressor nebulizer and particularly to a medical mechanical compressor nebulizer that has a medicine cup screwed on an air compression device to allow compressed air to enter an atomization device to generate atomization effect and discharge through an output device for therapeutic use.

BACKGROUND OF THE INVENTION

Modern epidemics disease science indicates that more than 70% of human diseases are environment-related. The human health system that is most directly affected by the environment is the respiratory system. Dry air tends to cause loss of water in the respiratory system, lower mucus secretion, and deceased activity of fine body hairs. The germicidal function of human body also degenerates. Immunity drops significantly. As a result, respiratory illnesses are prone to occur. In addition, people tend to feel fatigue, eyesight becomes poorer, and dizziness happens.

As known, the above diseases owing to the respiratory system, can be treated by sorts of medical mechanical compressor nebulizers. In addition to the general desktop models, portable models of a smaller size to be carried by users also have been developed to meet users' different needs.

Conventional medical mechanical compressor nebulizer generally has an atomization device, which is latched on an air compression device of the compressor nebulizer. The latching means is difficult to position and secure and possesses air leakage concerns. As a result, the compressed air cannot efficiently and effectively flow to the atomization device, resulting in poor quality of atomization and the therapeutic effect is thus compromised.

SUMMARY OF THE INVENTION

Therefore the primary object of the invention is to resolve the aforesaid disadvantages. The improved medical mechanical compressor nebulizer of the invention has an atomization device connected to the air compression device by a screwing mechanism. It effectively overcomes the problems of poor positioning and air leakage commonly seen with conventional medical mechanical compressor nebulizers.

Another object of the invention is to allow the air compression device and the atomization device to screw together and form an air chamber as a buffer space so that the compressed air is more stable, noise can be reduced, and the automization effect can be improved.

Yet another object of the invention is to provide a safety switch between the air compression device and the atomization device to prevent the apparatus from being inadvertently activated by the user accidentally depressing the power switch when the atomization device is not properly secured.

Still another object of the invention is to provide at least one filter in the air compression device to prevent filthy external objects from entering the air compression device and maintain the cleanness of the compressed air, and also to filter discharged air from the air compression device to maintain its cleanness.

In order to achieve the foregoing objects and enhance the therapeutic results through effective atomization of liquid inhalation dose, the improved medical mechanical compressor nebulizer comprises a body, an air compression device located in the body, a safety switch which is serially connected to voltage is located at the surrounding of the air compression device and an atomization device connecting to the air compression device and an output device. The atomization device is precisely and securely fastened to the air compression device by a screwing mechanism, not only for connection of air passage, but also for forming a coupled air chamber serving as a buffer to attain more stabilized ejecting air, reduce noise and achieve improved atomization effect. Also, the above screwing design can prevent the apparatus from being inadvertently activated by the user when the power switch is depressed accidentally.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENT

Figure 1:
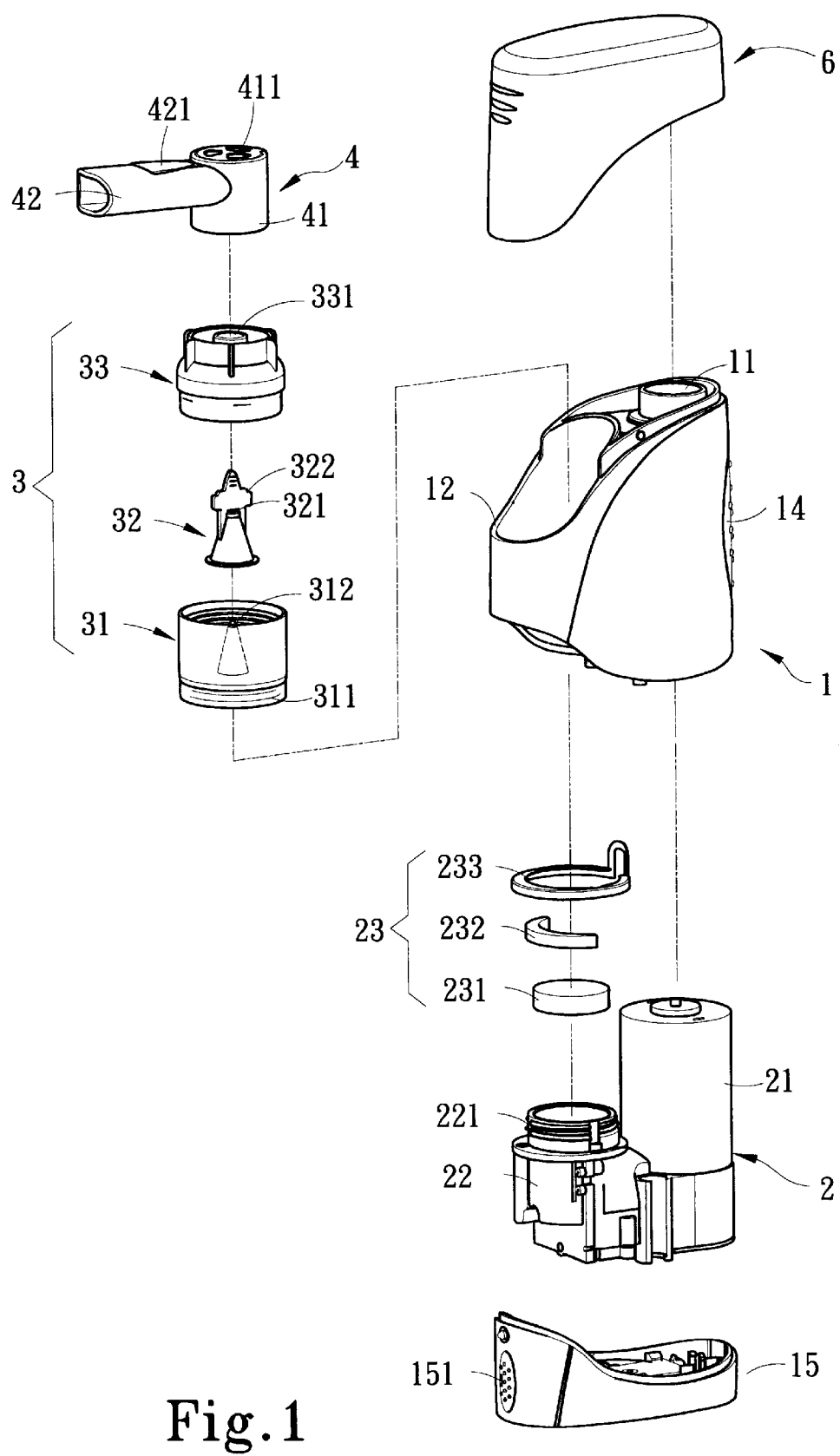
FIG. 1 is an exploded view of the invention.
Figure 2:
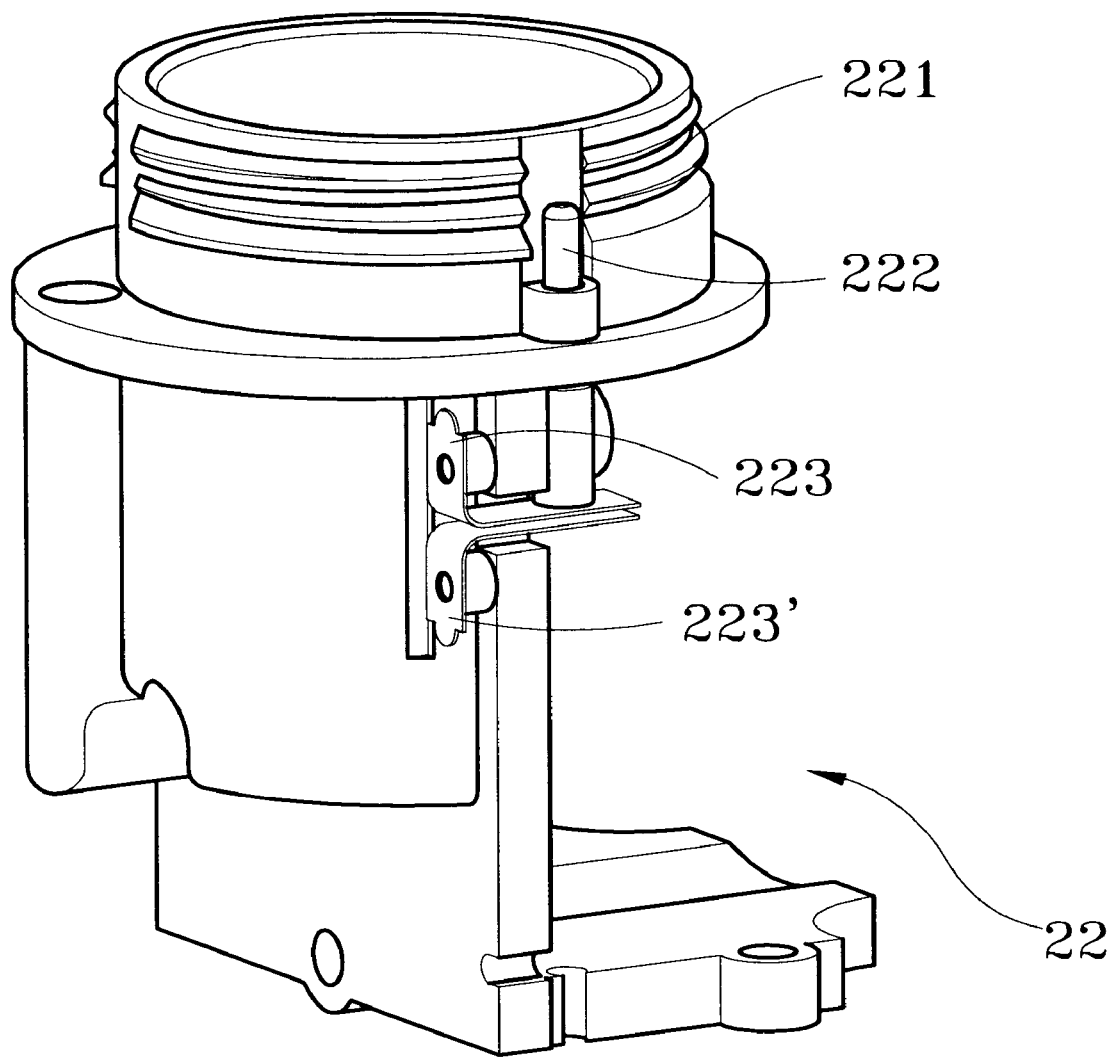
FIG. 2 is a perspective view of the safety switch of the invention.
Figure 3:
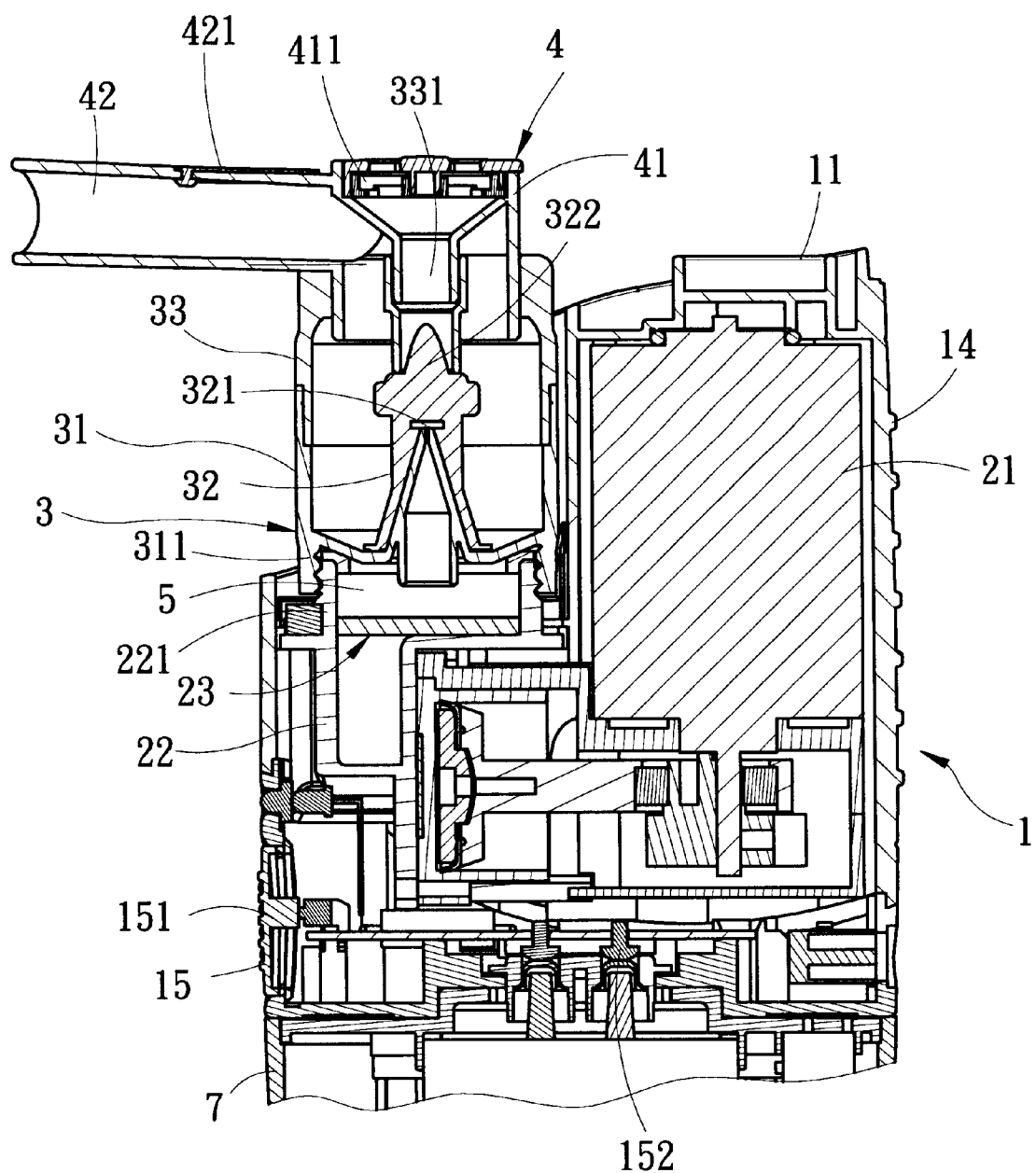
FIG. 3 is a sectional view of the invention.
Figure 4:
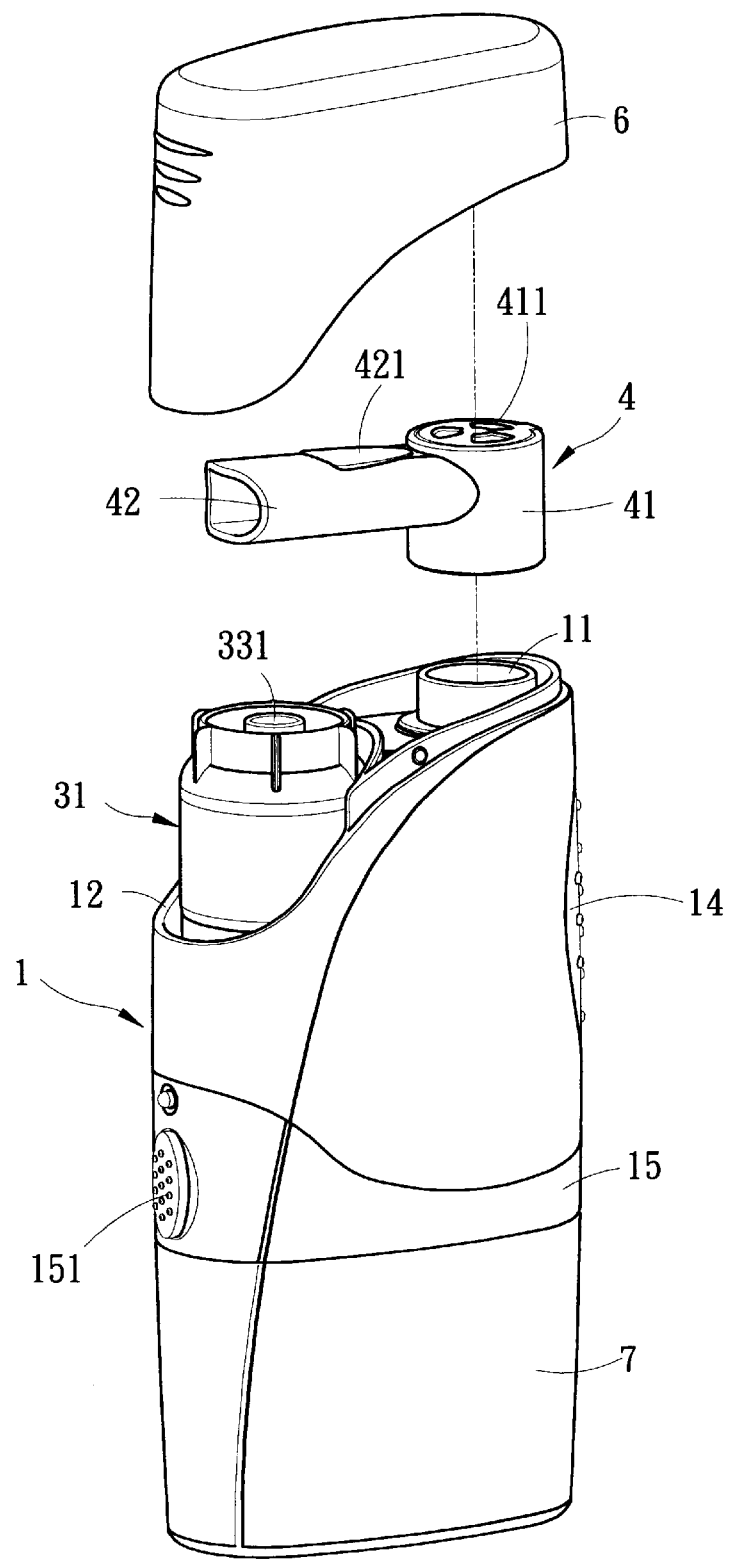
FIG. 4 is a perspective view of the invention.
Figure 5:
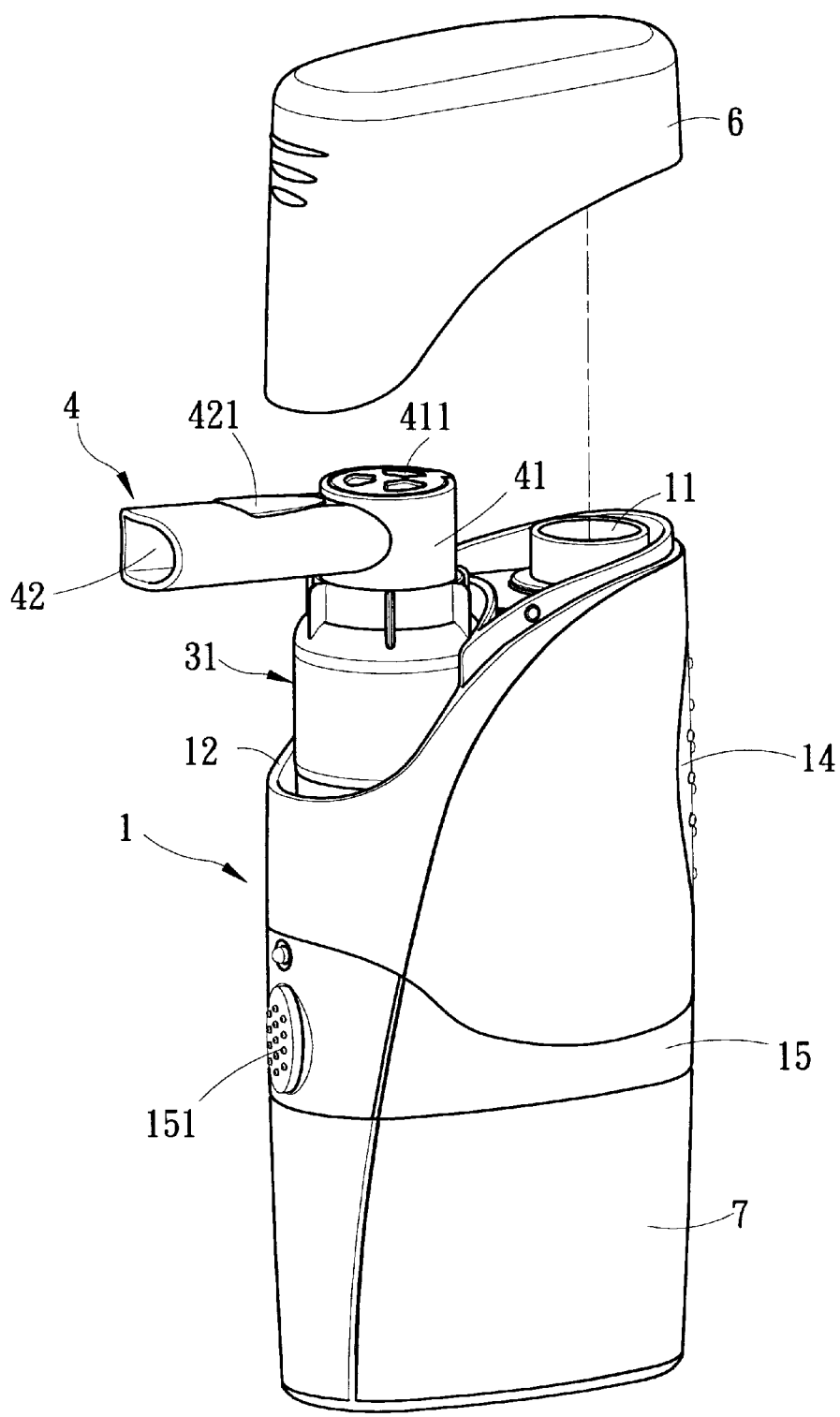
FIG. 5 is a perspective view of the invention in use.

Referring to FIGS. 1, 3, 4 and 5, the improved medical mechanical compressor nebulizer of the invention aims at generating atomization for liquid inhalation dose to fully achieve the desired therapeutic effect. It mainly includes a body 1, an air compression device 2 located in the body 1, an atomization device 3 for containing liquid inhalation dose and connecting with the air compression device 2 and the output device 4. The air compression device 2 compresses air rapidly and sends the compressed air to the atomization device 3. The atomization device 3 generates atomization effect for the liquid inhalation dose contained therein by the pressure difference principle and the siphonic principle. The atomized medicine is delivered through the output device 4 for therapeutic use.

The body 1 has one end forming an output device depositing means 11 for accommodating the output device 4, an inspecting section 12 corresponding to where the atomization device 3 is located to enable the user to see the amount of the medicine contained therein, the body 1 further has a slip-proof section 14 formed on another side to allow the users to grasp the body 1 securely during use, and; a bottom seat 15 which has a power switch 151 located on the surface for activating the air compression device 2. The bottom seat 15 further has a conductive section 152.

The air compression device 2 is located in the body 1. It mainly includes an actuator 21 and an air storage tank 22 for reducing operation noise of the air compression device 2. The air storage tank 22 has one end with a screw thread section 221 for fastening to the atomization device 3. Moreover, the air storage tank 22 further includes an air filter device 23 which has an air discharge filter 231 and an air intake filter 232. The air intake filter 232 is used to prevent filthy external objects from entering the air compression device 2 and contaminate the air source. The air discharge filter 231 filters the air flowing into the coupled air storage tank 22 and the atomization device 3 in order to maintain the cleanness of discharged air. In addition, the air filter device 23 has a detachable air intake filter anchor means 233 for holding the air intake filter 232 on the air storage tank 22, as well as facilitating its replacement process.

The atomization device 3 includes a medicine cup 31 which may be screwed onto the screw thread section 221 of the air storage tank 22, a spray nozzle 32 and a cap 33. The medicine cup 31 may, but not necessarily be transparent or translucent to enable the user to see the amount of medicine contained in the medicine cup 31. The bottom of the medicine cup 31 has a fastening section 311 corresponding to the screw thread section 221 of the air storage tank 22. When the fastening section 311 and the screw thread section 221 are screwed together in an up and down manner, a coupled air chamber 5 is formed to serve as a buffer space so that the air pressure output from the air compression device 2 to the atomization device 3 is more stable, and noise may also be reduced. The medicine cup 31 further has a tubular section 312 communicating with the coupled air chamber 5. The tubular section 312 is covered by the spray nozzle 32. The spray nozzle 32 has an upper side forming a support rack 322 and an air vent 321. The cap 33 is mounted onto the medicine cup 31 and has an air passage 331 in the center.

The output device 4 is deposited on the cap 33 of the atomization device 3. It includes an input section 41 and an output section 42. There is an air intake valve 411 located on the upper side of the input section 41, the input section 41 will open to let air in to mix with atomization when the user holds the output section 42 in the mouth and inhales to enhance the therapeutic effect. The output section 42 has an air discharge valve 421 located on the surface thereof to discharge the exhaled air or the waste air when the user coughs severely.

By means of the construction set forth above, the atomization device 3 may be fastened to the air compression device 2 precisely and securely, and form the coupled air chamber 5 which serves as a buffer space to stabilize the ejecting air pressure, reduce noise and better achieve the desired atomizing effect. It thus can overcome the problems of difficult positioning caused by latching of the medicine cup on the air compression device 2, unsecured anchoring and poorer atomization that occur with conventional atomizers.

Referring to FIG. 2, the air storage tank 22 has two conductive plates 223 and 223' located inside. The conductive plates 223 and 223' are serially connected to the power switch 151, and the conductive plates 223 and 223' are interposed by a safety valve 222 so that when the atomization device 3 is fastened to the air storage tank 22, the bottom of the atomization device 3 depresses the safety valve 222 to make the conductive plates 223 and 223' contact each other and short. Therefore, when the atomization device 3 is not properly fastened, the conductive plates 223 and 223' will not make contact with each other and the result is an open circuit. It prevents the user from inadvertently activating the therapeutic apparatus if the atomization device 3 is not properly fastened.

When the apparatus of the invention is not in use, the output device 4 may be mounted on the output device depositing means 11, a protective cap 6 may be used to cover the body 1 where the output device 4 and the medicine cup 3 are exposed to maintain the cleanness inside the body 1.

Furthermore, the base seat 15 may have a conductive section 152 to connect to the battery power source 7 or commercial AC power (not shown in Figures).

What is claimed is:

1. An improved medical mechanical compressor nebulizer for atomizing liquid inhalation dose to achieve therapeutic effect, characterized by:

a body;

an air compression device located in the body having an actuator and an air storage tank to reduce operation noise of the air compression device, the air storage tank having one end formed a screw thread section and a safety switch which is serially connected to voltage located therein;

an atomization device including a medicine cup which has a tubular section, a spray nozzle covering the tubular section and a cap covering the medicine cup, the medicine cup having a bottom formed a fastening section corresponding and fastening to the screw thread section of the air storage tank to form a coupled air chamber; and an output device connected to the atomization device for delivering atomizing liquid inhalation dose;

wherein the atomization device is connected securely to the air compression device by screwing to form the coupled air chamber and to activate the safety switch, thereby attaining more stabilized ejecting air, reducing noise, enhancing atomization effect and preventing accidental activation of the apparatus by the user.

2. The improved medical mechanical compressor nebulizer of claim 1, wherein the safety switch includes two conductive plates being interposed by a safety valve.

3. The improved medical mechanical compressor nebulizer of claim 1, wherein the output device can be located on the cap of the medicine cup or on the output device depositing means of the body.

4. The improved medical mechanical compressor nebulizer of claim 1, wherein the air compression device includes an air filter device.

5. The improved medical mechanical compressor nebulizer of claim 4, wherein the air filter device includes an air discharge filter and an air intake filter.

6. The improved medical mechanical compressor nebulizer of claim 4, wherein the air filter device includes a detachable air discharge filter anchor means.

* * * * *